US00PP13541P2

(12) United States Plant Patent
Morgan

(10) Patent No.: US PP13,541 P2
(45) Date of Patent: Feb. 4, 2003

(54) ARGYRANTHEMUM PLANT NAMED 'COBSING'

(75) Inventor: Mal Morgan, Macquarie Fields (AU)

(73) Assignee: Nuflora International Pty. Ltd., New South Wales (AU)

( * ) Notice: Subject to any disclaimer, the term of this patent is extended or adjusted under 35 U.S.C. 154(b) by 0 days.

(21) Appl. No.: 09/996,381

(22) Filed: Nov. 30, 2001

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A new and distinct cultivar of Argyranthemum plant named 'Cobsing', characterized by its compact, mounded, upright and outwardly spreading plant habit; freely branching habit; freely flowering habit with numerous inflorescences per plant; single daisy inflorescence form; and pink-colored ray florets.

1 Drawing Sheet

BOTANICAL CLASSIFICATION/CULTIVAR DENOMINATION

*Argyranthemum frutescens* cultivar Cobsing.

BACKGROUND OF THE INVENTION

The present invention relates to a new and distinct cultivar of Argyranthemum plant, botanically known as *Argyranthemum frutescens* and hereinafter referred to by the name 'Cobsing'.

The new Argyranthemum is a product of a planned breeding program conducted by the Inventor in Cobbitty, New South Wales, Australia. The objective of the program is to create and develop new compact Argyranthemum cultivars with numerous inflorescences and attractive ray floret coloration.

The new Argyranthemum originated from a cross by the Inventor of two unidentified selections of *Argyranthemum frutescens,* not patented. The new Argyranthemum was discovered and selected by the Inventor as a plant within the progeny of the stated cross in a controlled environment in Cobbitty, New South Wales, Australia in 1998. The selection of the new Argyranthemum was based on its single daisy inflorescence form and pink-colored ray florets.

Asexual reproduction of the new Argyranthemum by terminal cuttings taken in a controlled environment in Cobbitty, New South Wales, Australia since 1998, has shown that the unique features of this new Argyranthemum are stable and reproduced true to type in successive generations.

SUMMARY OF THE INVENTION

The new Argyranthemum has not been observed under all possible environmental conditions. The phenotype may vary somewhat with variations in environment such as temperature and light intensity without, however, any variance in genotype.

The following characteristics have been repeatedly observed and are determined to be basic characteristics of 'Cobsing' and distinguish the new Argyranthemum as a new and distinct cultivar:

1. Compact, mounded, upright and outwardly spreading plant habit.
2. Freely branching habit, dense and bushy plants.
3. Freely flowering habit with nemerous inflorescences per plant.
4. Single daisy inflorescence form.
5. Pink-colored ray florets.

Plants of the new Argyranthemum differ from plants of the parent selections primarily in ray floret coloration.

Plants of the new Argyranthemum can be compared to plants of the cultivar Summer Pink, not patented. In side-by-side comparisons conducted in Encinitas, Calif., plants of the new Argyranthemum differed from plants of the cultivar Summer Pink in the following characteristics:

1. Plants of the new Argyranthemum were more compact than plants of the cultivar Summer Pink.
2. Plants of the new Argyranthemum had smaller inflorescences than plants of the cultivar Summer Pink.

BRIEF DIESRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Argyranthemum.

The photograph at the top of the sheet comprises a side perspective view of a typical flowering plant of 'Cobsing' grown in a 20-cm container.

The photograph at the bottom of the sheet comprises a close-up view of typical leaves, an inflorescence bud, developing inflorescences and a fully opened inflorescence of 'Cobsing'.

DETAILED BOTANICAL DESCRIPTION

The aforementioned photographs, following observations and averaged measurements describe plants grown in Encinitas, Calif., in an outdoor nursery under full sunlight during the late winter and early spring with day temperatures averaging 18° C. and night temperatures averaging 13° C.

Plants were grown for about 16 weeks in 20-cm containers with one plant per container. Plants were pinched one time about five weeks after planting. Color references are made to The Royal Horticultural Society Colour Chart, version 1995, except where general terms of ordinary dictionary significance are used.

Botanical classification: *Argyranthemum frutescens* cultivar Cobsing.

Parentage:

*Female or seed parent.*—Unidentified selection of *Argyranthemum frutescens,* not patented.

*Male or pollen parent.*—Unidentified selection of *Argyranthemum frutescens,* not patented.

Propagation:

*Type.*—Terminal vegetative cuttings.

*Time to initiate roots.*—About 10 days at 20° C.

*Time to produce a rooted cutting.*—About 21 days at 20° C.

*Root description.*—Fine, fibrous and freely branching.

Plant description:

*General appearance.*—Inverted triangle; compact, mounded, upright and outwardly spreading plant form with dense foliage and inflorescences held above the foliage on long peduncles. Moderately vigorous growth habit.

*Plant height.*—About 28 cm.

*Plant width.*—About 44 cm.

*Lateral branch description.*—Quantity per plant: About 10. Length: About 22 cm. Diameter: About 3.5 mm. Internode length: About 1.1 cm. Aspect: Upright and outwardly spreading. Texture: Smooth, glabrous. Color: 138C.

*Foliage description.*—Arrangement: Alternate, simple. Quantity per lateral branch: About 20. Length: About 5 cm. Width: About 3.8 cm. Shape: Pinnatifid, deeply divided. Apex: Acute. Base: Attenuate. Margin: Entire; deeply incised. Texture, both surfaces: Smooth, glabrous; waxy. Venation pattern: Pinnate. Petiole length: About 2 cm. Petiole diameter: About 3 mm. Petiole texture: Smooth. Color: Young and fully expanded foliage, upper surface: 137B. Young and fully expanded foliage, lower surface: 137C. Venation, upper and lower surfaces: 137C. Petiole, upper and lower surfaces: 137C.

Inflorescence description:

*Appearance.*—Single daisy composite inflorescence form with ligulate ray florets. Inflorescences held upright on terminal and axillary peduncles. Disc and ray florets arranged acropetally on a capitulum. Inflorescences pesistent. Inflorescences fragrant; sour. Inflorescences last about four to seven days on the plant.

*Flowering response.*—Under natural conditions, plant flower from spring to early fall; plants flower continuous during this period.

*Quantity of inflorescences.*—Very freely flowering; about 25 buds and inflorescences per lateral branch and about than 250 buds and inflorescences per plant.

*Inflorescence size.*—Diameter: About 3.4 cm. Depth (height): About 8 mm. Diameter of disc: About 1.2 cm.

*Inflorescence buds, at stage of showing color.*—Height: About 1 cm. Diameter: About 7 mm. Shape: Roughly spherical to ovoid with development. Color: 75C to 75D.

*Ray florets.*—Quantity per inflorescence: About 15 arranged in a single whorl. Shape: Ligulate. Length: About 1.6 cm. Width: About 5 mm. Apex: Emarginate. Base: Acute. Margin: Entire. Texture, upper and lower surfaces: Smooth, satiny. Aspect: Initially upright; when mature, about 90° from vertical. Color: When opening, upper surface: 75D. When opening, lower surface: 75C. Fully opened, upper surface: 75C; fading to 75D with subsequent development. Fully opened, lower surface: 76D.

*Disc florets.*—Arrangement: Massed at the center of the inflorescence. Quantity per inflorescence: About 180. Shape: Tubular, five-parted at apex; apex, acute; base, fused. Length: About 5 mm. Diameter: At apex: About 1.5 mm. At base: About 1 mm. Color: Immature: Apex: 12A. Mid-section and base: 1C. Mature: Apex: 14A. Mid-section and base: 1C.

*Involucral bracts* (*phyllaries*).—Appearance: Scale-like; margins, papery. Quantity per inflorescence: About 30. Length: About 6 mm. Width: About 3 mm. Shape: Broadly elliptic. Apex: Acute. Base: Truncate. Margin: Entire. Texture, upper and lower surfaces: Glabrous, smooth. Color: Upper surface: 138D. Lower surface: 138C.

*Peduncle.*—Strength: Moderately strong; wiry. Aspect: Upright to about 90° from vertical. Length: First peduncle: About 7 cm. Fourth peduncle: About 8.5 cm. Seventh peduncle: About 10 cm. Diameter: About 1.5 mm. Texture: Smooth, glabrous. Color: 147B to 147C.

*Reproductive organs.*—Androecium: Present on disc florets only. Quantity per floret: Five fused around style. Anther shape: Ovoid. Anther length: Less than 1 mm. Anther color: 12A. Amount of pollen: Scarce. Pollen color: 12A. Gynoecium: Quantity per floret: One. Pistil length: About 5 mm. Stigma shape: Two-parted. Stigma color: 12A. Style length: About 3 mm. Style color: 1D. Ovary color: 155A. Seed/fruit: Seed and fruit production has not been observed.

Disease/pest resistance: Resistance to pathogens and pests common to Argyranthemums has not been observed on plants grown under commercial conditions.

Temperature/weather tolerance: Plants of the new Argyranthemum have been observed to be tolerant to rain, wind and to temperatures from 0° to 30° C.

It is claimed:

1. A new and distinct cultivar of Argyranthemum plant named 'Cobsing', as illustrated and described.

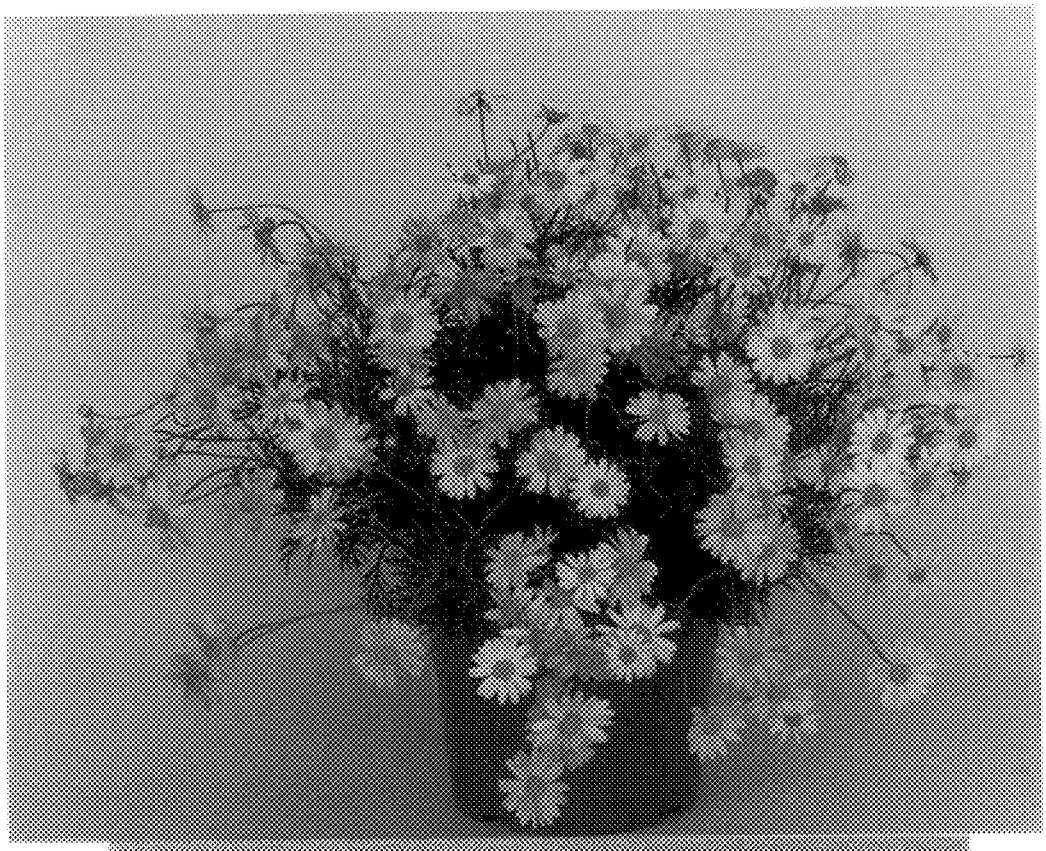
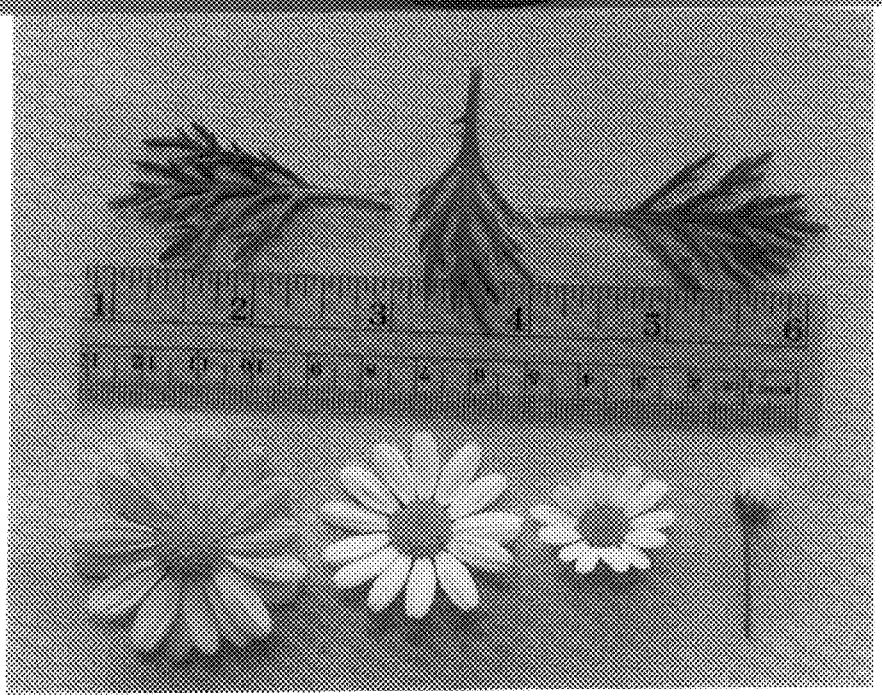

* * * * *